(12) United States Patent
Bellafiore et al.

(10) Patent No.: US 6,395,915 B1
(45) Date of Patent: May 28, 2002

(54) METHOD FOR PRODUCING PURIFIED TOCOTRIENOLS AND TOCOPHEROLS USING LIQUID CHROMATOGRAPHY

(75) Inventors: Louis Bellafiore, Wilmette; Kevin Henretta, Chicago, both of IL (US)

(73) Assignee: Technikrom, Inc., Evanston, IL (US)

( * ) Notice: Subject to any disclaimer, the term of this patent is extended or adjusted under 35 U.S.C. 154(b) by 0 days.

(21) Appl. No.: 09/657,718

(22) Filed: Sep. 8, 2000

Related U.S. Application Data

(60) Provisional application No. 60/153,308, filed on Sep. 10, 1999.

(51) Int. Cl.[7] ................................................. C11B 3/10
(52) U.S. Cl. ........................................ 554/193; 554/191
(58) Field of Search .................................. 554/191, 193

(56) References Cited

U.S. PATENT DOCUMENTS

| | | | |
|---|---|---|---|
| 4,122,094 A | 10/1978 | Woziwozki | 260/345.6 |
| 5,157,132 A | 10/1992 | Tan et al. | 549/413 |
| 5,190,618 A | 3/1993 | Top et al. | 549/413 |
| 5,908,940 A | 6/1999 | Lane et al. | 549/413 |

FOREIGN PATENT DOCUMENTS

| | | | |
|---|---|---|---|
| EP | 0 333 472 | | 9/1989 |
| EP | 083174 | * | 3/2001 |
| WO | WO 99/38859 | | 8/1999 |
| WO | WO 99/38860 | | 8/1999 |
| WO | WO 00/43095 | | 7/2000 |

OTHER PUBLICATIONS

European Patent Office—Search Report—Jan. 25, 2001.
Publication: Barrie Tan and Linda Brzuskiewicz Separation of Tocopherol and Tocotrienol Isomers Using Normal and Reverse Phase Liquid Chromatography.
Hoehler et al., Journal of Agric. Food Chem., vol. 46, pp. 973–978, 1998.*

* cited by examiner

Primary Examiner—Deborah D. Carr
(74) Attorney, Agent, or Firm—William T. Rifkin; Thomas W. Ryan; Piper Marbury Rudnick & Wolfe (57) ABSTRACT

A method separating tocotrienols from tocopherols and the isomers thereof on a large-scale or commercially feasible basis. Separation is accomplished using reverse phase partition liquid chromatography. The chromatography column is prepared using a stationary phase comprising a hydrophobic or aromatic reverse phase chromatography media. The mobile phase consists of a solvent which is capable of solubilizing the crude stock, tocotrienols and tocopherols. The chromatography column containing the stationary and mobile phases is loaded with a crude feed stock and the tocotrienols, tocopherols and/or isomers thereof are eluted at a predetermined linear velocity.

19 Claims, 8 Drawing Sheets

METHOD FOR PRODUCING PURIFIED TOCOTRIENOLS AND TOCOPHEROLS USING LIQUID CHROMATOGRAPHY

CLAIM OF PRIORITY

This application claims priority from U.S. Provisional Patent Application Ser. No. 60/153,308, filed Sep. 10, 1999.

BACKGROUND OF THE INVENTION

1. Field of Invention

The present invention relates generally to a method of producing commercially feasible amounts of purified tocotrienols, tocopherols and isomers thereof or crude stocks enriched in tocotrienols or tocopherols using reverse phase liquid chromatography.

2. Description of Prior Art

Tocopherol is used widely as an antioxidant with applications in the cosmetic, pharmaceutical. nutraceutical, food and fine chemical industries. The four main isomers of tocopherol (alpha, beta, delta, and gamma) are generally referred to individually and as a group as "Vitamin E." Tocotrienols are structurally very similar to tocopherols and also have four main isomers (alpha, beta, delta, and gamma). Tocotrienols have been shown to provide a significant increase in antioxidant activities over tocopherols. Recent studies have indicated that tocotrienols, and to a somewhat lesser extent tocopherols, provide certain health benefits, including reduction in serum cholesterol levels and prevention of coronary heart disease due to their antioxidant properties. When produced or otherwise isolated, tocotrienols and tocopherols, due to their similarity, can be found together. Therefore, separation of these two classes of chemical compounds is necessary to evaluate or produce individual classes of these materials.

There are several methods known in the art that can be used to concentrate and/or purify tocotrienols and tocopherols from crude mixtures containing them. Common chemical separation methods include extraction, distillation (fractional distillation and molecular distillation), membrane filtration and chromatography. Within chromatography, there are several general subcategories including adsorption chromatography, partition chromatography, ion exchange chromatography, and size exclusion chromatography that can be applied.

The prior art contains several previously developed and published liquid chromatography methods directed toward the separation of tocotrienols and tocopherols. Some of these methods are designed only for the qualitative and quantitative analysis of tocotrienols and tocopherols and are not suitable for process cliromatography (the use of chromatography to isolate and recover substantial amounts of pure material from a mixture on a commercial scale). Other methods are designed for preparative work but do not provide a discrete separation between all of the isomers of tocotrienols and all of the isomers of tocopherols into two different groups of eluting material.

Prior art liquid chromatography methods, particularly those described below, can thus be broken into two categories: analytical liquid chromatography methods designed to resolve the different components at very low levels to permit analysis with bench top analytical HPLC equipment; and preparative (process) liquid chromatography methods designed for the commercial purification of specific components out of a crude feedstock. The priori art does not describe a reverse-phase partition liquid chsomatography method which can be used commercially to purify tocotrienols and/or tocopherols, or further, to provide one simple method to separate all of the tocopherol isomers n d all o f the tocotrienol isomers at the same time.

U.S. Pat. No. 4,122,094 to Woziwodzki detail s a method of separating the isomers of tocopherol by liquid/solid chromatography. The method of Woziwodzki is directed to analytical separations of tocopherol isomers through the use of normal phase media rather than large-scale separations useful for commercial production. Woziwodzki also does not discuss using the disclosed methods to separate tocopherols from tocotrienols or separating the isomers of tocotrienol.

U.S. Pat. No. 5,157,132 to Tan et al. describes an integrated process for recovery of carotenoid and tocotrienols from vegetable oils. This method uses normal phase absorption chromatography in which components in the crude material bind, sometimes irreversibly, to the stationary phase. The lifetime of normal phase media is generally much shorter than that of reversed phased media. As Such, the economics of larger scale processes can be significantly affected because the stationary phase must be replaced frequently and additional man-hours are expended. Furthermore, the surface of underivatized silica, which is typically used for normal phase chromatography, is very sensitive to water (from air, solvents and crude material) which deactivates the stationary phase surface resulting in non uniform elution profiles. This can make automation difficult and production unpredictable. The method of U.S. Pat. No. 5,157,132 also uses hexane as the mobile phase. These solvents are more hazardous and more expensive (including the cost of disposal) than other mobile phase solvents, such as ethanol and water. Finally, this reference does not teach a method of separating tocopherols from tocotrienols.

Top et al. teach a method of production of high concentration tocopherols and tocotrienols from palm-oil by-products through ion-exchange chromatography in U.S. Pat. No. 5,190,618. Ion-exchange chromatography separates based on the retention of charged molecules on a charged stationary phase rather than on the attraction of molecules to an aromatic and/or hydrophobic stationary phase. The major shortcoming of the method outlined in this patent is that it does not provide a high degree of resolution and further does not even show separation between the tocopherols and tocotrienols in the crude material.

U.S. Pat. No. 5,908,940 discloses a process for recovering tocotrienols, tocopherols and tocotrienol-like compounds. The method taught utilizes chemical extractions. While likely useful for small-scale applications, the patent does not discuss how the method can be used for large scale recovery needed in commercial operations. The patent also does not teach use of the disclosed method for separation of the separate isomers of tocotrienols and tocopherols.

It is therefore one object of the present invention to provide a method to isolate, with high purity if required, all of the different isomers of tocotrienols and tocopherols. It is a further object of the present invention to isolate, on any required scale (grams, kilograms, tons), the desired products. It is yet another object of the invention to provide a method of "class separation" of tocotrienols from tocopherols on a commercial scale through the use of either a single column reverse phase chromatography process or a multiple column simulated moving bed (SMB) reverse phase chromatography process due to the binary nature of separation which is amenable to SMB. It is an additional object of the present invention to provide a separation method which utilizes inexpensive and safe mobile phase solvents.

DESCRIPTION OF PREFERRED EMBODIMENTS

Described herein is a reverse phase partition chromatography method that utilizes alcohol or acetonitrile solvent systems without the addition of salt, acid, or base modifiers to concentrate and purify tocotrienols and tocopherols. Normal phase chromatography operates on the basis of absorption and release of hydrophilically attracted moieties by using a polar stationary phase and a less polar mobile phase. Thus, hydrophobic compounds elute more quickly than do hydrophilic compounds. In contrast, reverse phase operates on the basis of a partitioning process between the mobile phase and the stationary phase directed by hydrophobic, aromatic or other types of attraction. For example, the more hydrophobic the stationary phase, the greater is the tendency of the column to retain hydrophobic moieties. In this case, hydrophilic compounds elute more quickly than do hydrophobic compounds.

Certain process parameters, such as loading capacity, physical properties of the stationary phase, and the linear velocity of the mobile phase may be varied depending on the desired purity of the end products. For example, a slightly enriched palm oil crude may be utilized to make a cooking oil or as a feed additive for livestock, whereas a highly purified form of a single isomer may provide significant medical benefit to humans and pets. The general method presented in this report can generate a final product containing tocotrienols or tocopherols at any purity desired up to 100%. As detailed below in the Process Examples, the instant method was used to generate final products at greater than 95% purity. It should also be noted that, regardless of the method of chromatographic separation used, including the instant method, natural or synthetic crude stocks may benefit from pre-chromatographic treatment, such as molecular distillation, to improve the efficiency of the chromatographic separation.

The functionality of the instant reverse phase liquid chromatography separation method depends on three elements: the stationary phase, the mobile phase, and the loading of the crude stock. As is discussed in greater detail below, the instant reverse phase chromatography method utilizes and maximizes the function of these three elements to achieve a novel method to obtain high quality, high quantity, and discrete separations of the isomers of tocotrienols and tocopherols. However, the method can also be used to produce less highly purified products or, if desired, enriched feed stocks.

I. Stationary Phase

In order to be used effectively in large-scale preparative liquid chromatography, the stationary phase must be robust, available in large quantities, and manufactured using a reproducible production method. In the preferred embodiment of the method, the stationary phase should provide selectivity related to the hydrophobic and/or aromatic differences between the tocotrienols and the tocopherols to provide class separation. It was therefore determined that reversed phase media containing either alkyl silanes and/or an aromatic character meet these requirements as they elute the tocotrienols as a group separate from the tocopherols.

Resolution of the individual isomers of tocotrienols and tocopherols depends on the shape and size of the liquid chromatography particles used and the make-up of the mobile phase, discussed below. In the preferred embodiment of the method, particles of 10 microns or larger should be used. Particles smaller than 10 microns cannot be practically used in large scale-separations due to high pressure generation, high cost, and general lack of availability. For either a "one-step" or "two-step" process, spherical or irregular particles in the range of 10 microns and larger should therefore be used, with a preferred range of between 10 to 200 microns. Common hydrophobic reverse phase chromatography supports including silica, polystyrene/divnylbenzene, polymethacrylate, and cellulose can be used for either a one-step or a two-step process. The liquid chromatography column is prepared using the selected mobile phase in any of the conventional manners know in the art. While any type of liquid chromatography column can be used, the use of a dynamic axial compression column (TechniKrom, Inc., Evanston, Ill.) provides the benefits of increased separation efficiency and significantly increased column bed lifetimes.

II. Mobile Phase

Usable mobile phases are determined by the limitations in the solubility of the end products and the crude material. The disclosed method can be carried out by means of any commonly used reverse phase chromatography solvent combined with water to form a mobile phase in which the end products and the crude stock are soluble. In the preferred embodiment of the method, a safer and less expensive solvent, such as ethanol, should be used. However, other alcohols, such as methanol, as well as solvents such as acetonitrile may be used. For large-scale separations, it is important that the solvents used in the mobile phase are of a grade that is cost effective and readily available in large quantities due to the large amount of solvent used. For this work, 190 proof USP ethanol and deionized water were used. It should be noted that as the level of water is increased, the solubility decreases, so therefore more than 30% water in the mobile phase should be avoided. Use of a gradient elution (increasing the amount of solvent in the blend over time) of the mobile phase rather than an isocratic elution (constant level of solvent through the run) of the mobile phase can be used to improve the separation of the end products.

The linear velocity of the mobile phase will also affect the separation and the amount of time required to elute the desired products. The use of a precision pumping system (TechniKrom, Inc., Evanston, Ill.) permits accurate flow rate control throughout the separation process. This allows automation of the process and guarantees a uniform flow rate to elute products in a reproducible fashion. The linear velocity or flow rate of the mobile phase should remain within acceptable chromatography norms. Chromatography theory shows that linear velocities should generally not be less than 10 cm/hour to avoid separation deterioration due to diffusion. The upper limits of linear velocity is generally dictated by the pressure limits of the columns, valves, tubing, and pumps used to deliver the mobile phase. However, even without pressure limitations, flow rates should not be more than 1000 cm/hour as inadequate chemical interaction between the products and the stationary phase surface may occur.

The following examples show how changes in the mobile phase affect the separation of tocotrienols and tocopherols and their isomers. This first example uses three isocratic runs (solvent content in mobile phase unchanged over time) with varying levels of the same solvent. The second example uses two identical gradient runs (solvent content in mobile phase increased over time) with different solvents. These examples are merely illustrative of the disclosed process.

Figure 1:
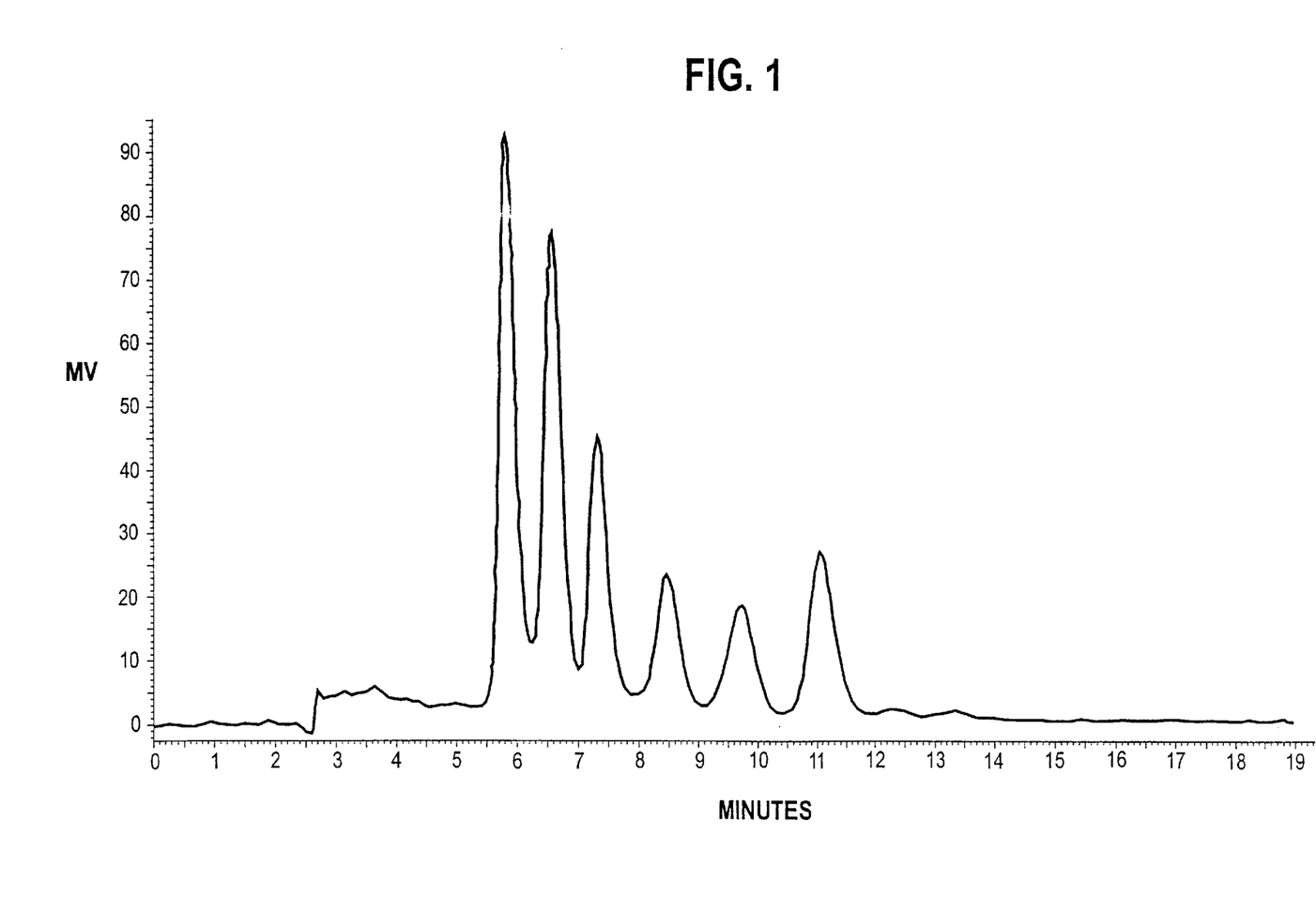
FIG. 1. is a chromatogram showing a separation using the disclosed method with a mobile phase comprised of 98% USP ethanol.
Figure 2:
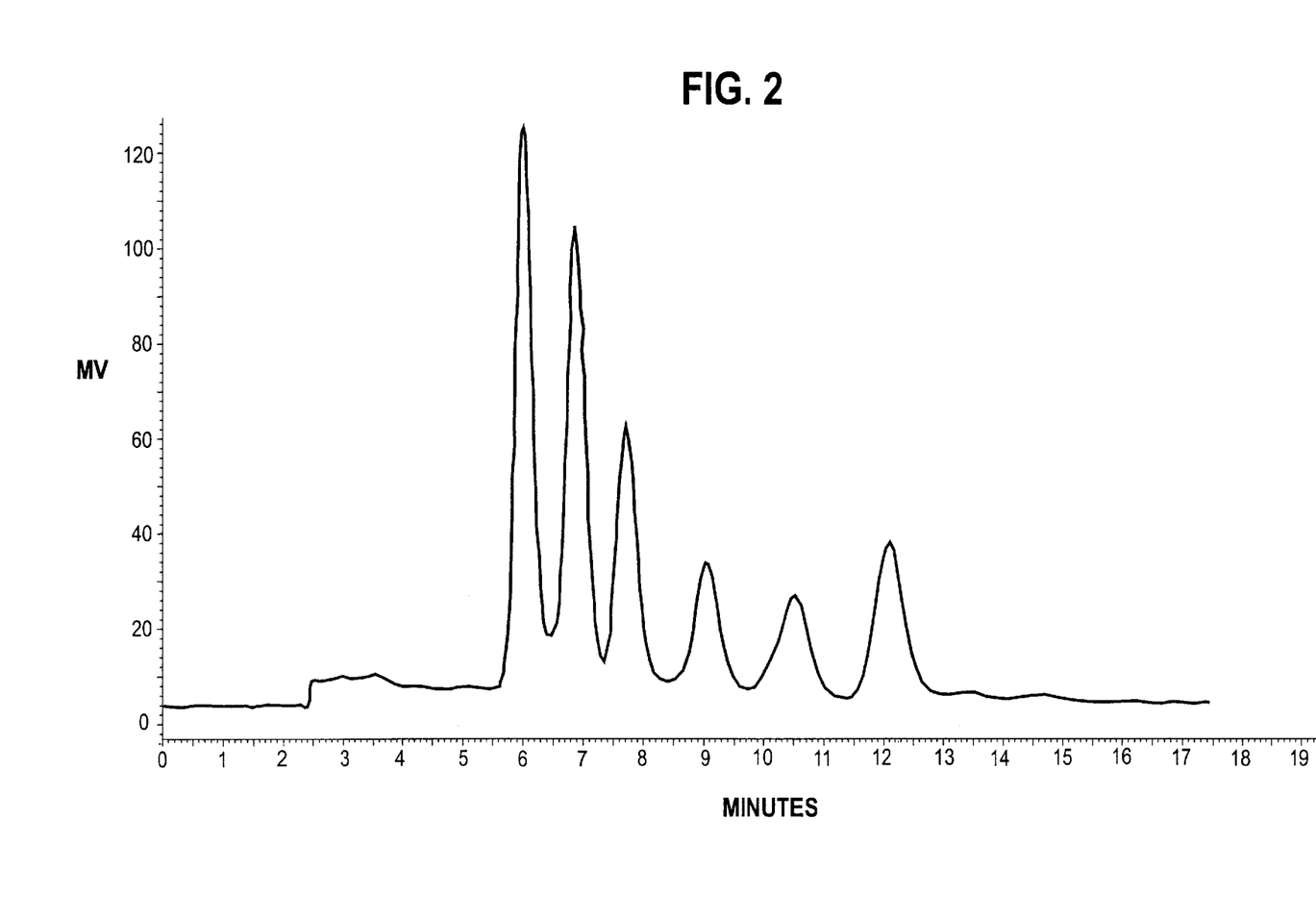
FIG. 2. is a chromatogram showing a separation using the disclosed method with a mobile phase comprised of 97% USP ethanol.
Figure 3:
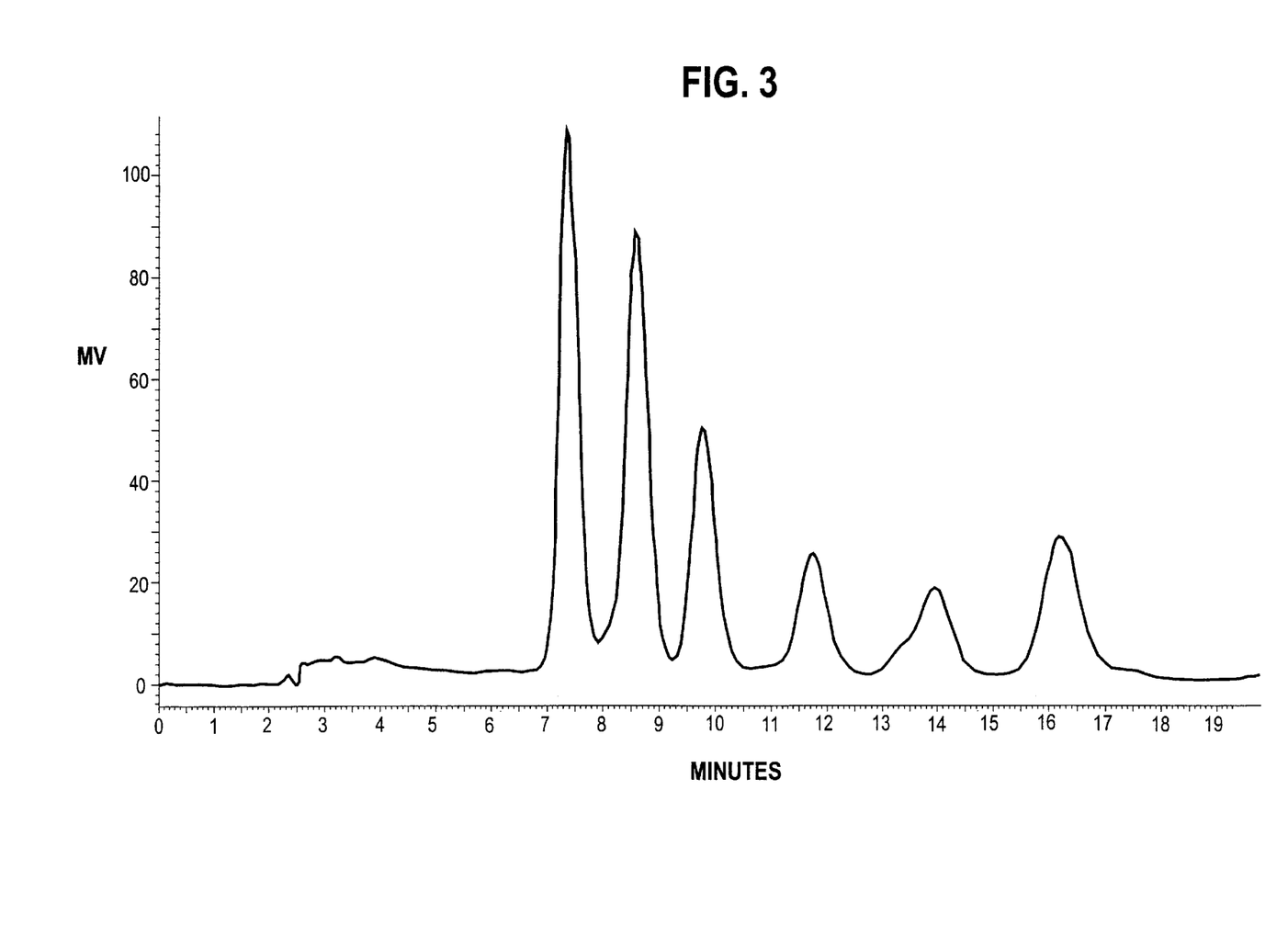
FIG. 3. is a chromatogram showing a separation using the disclosed method with a mobile phase comprised of 95% USP ethanol.
Figure 4:
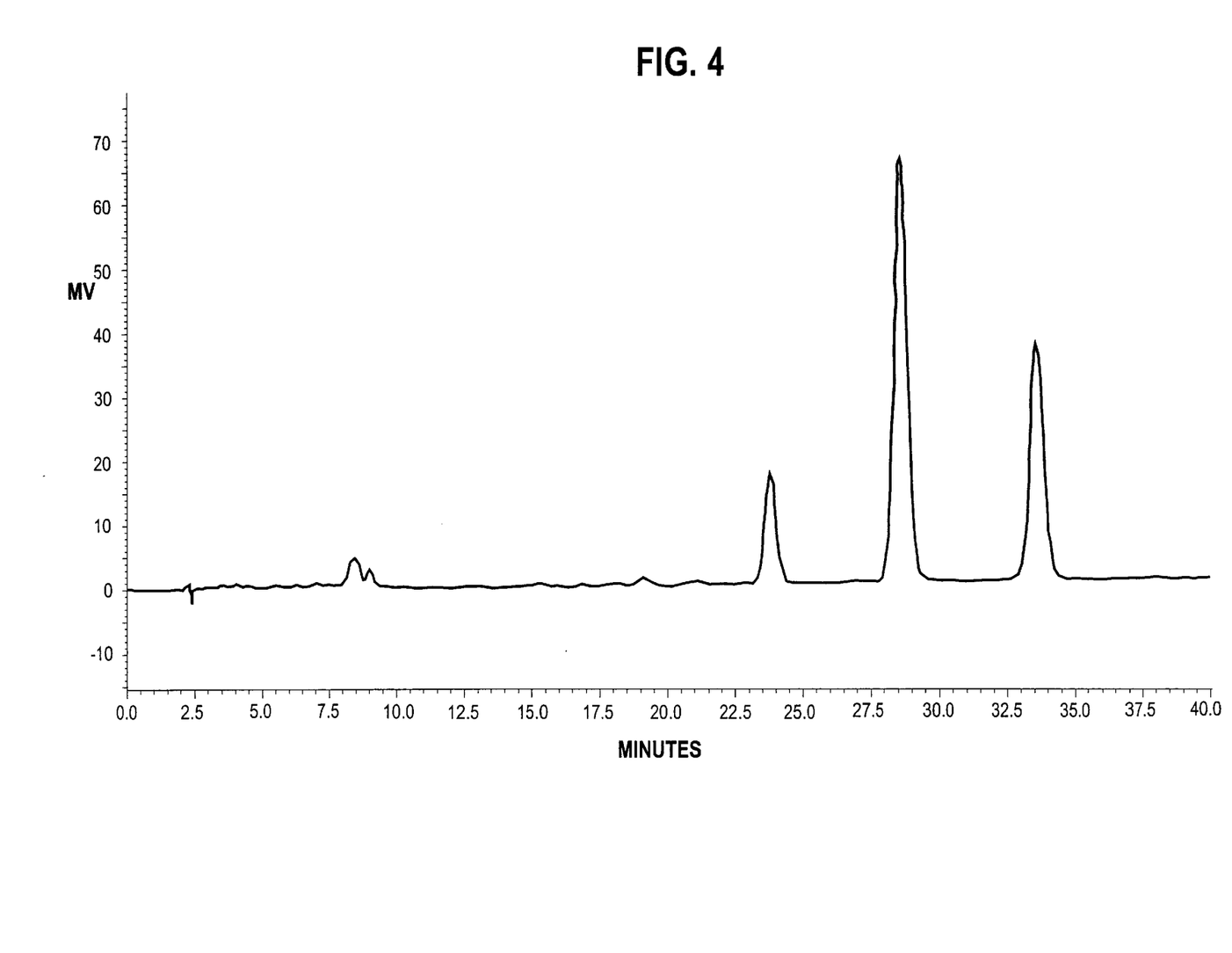
FIG. 4. is a chromatogram showing a separation using the disclosed method using 90% to 100% acetonitrile over 40 minutes.
Figure 5:
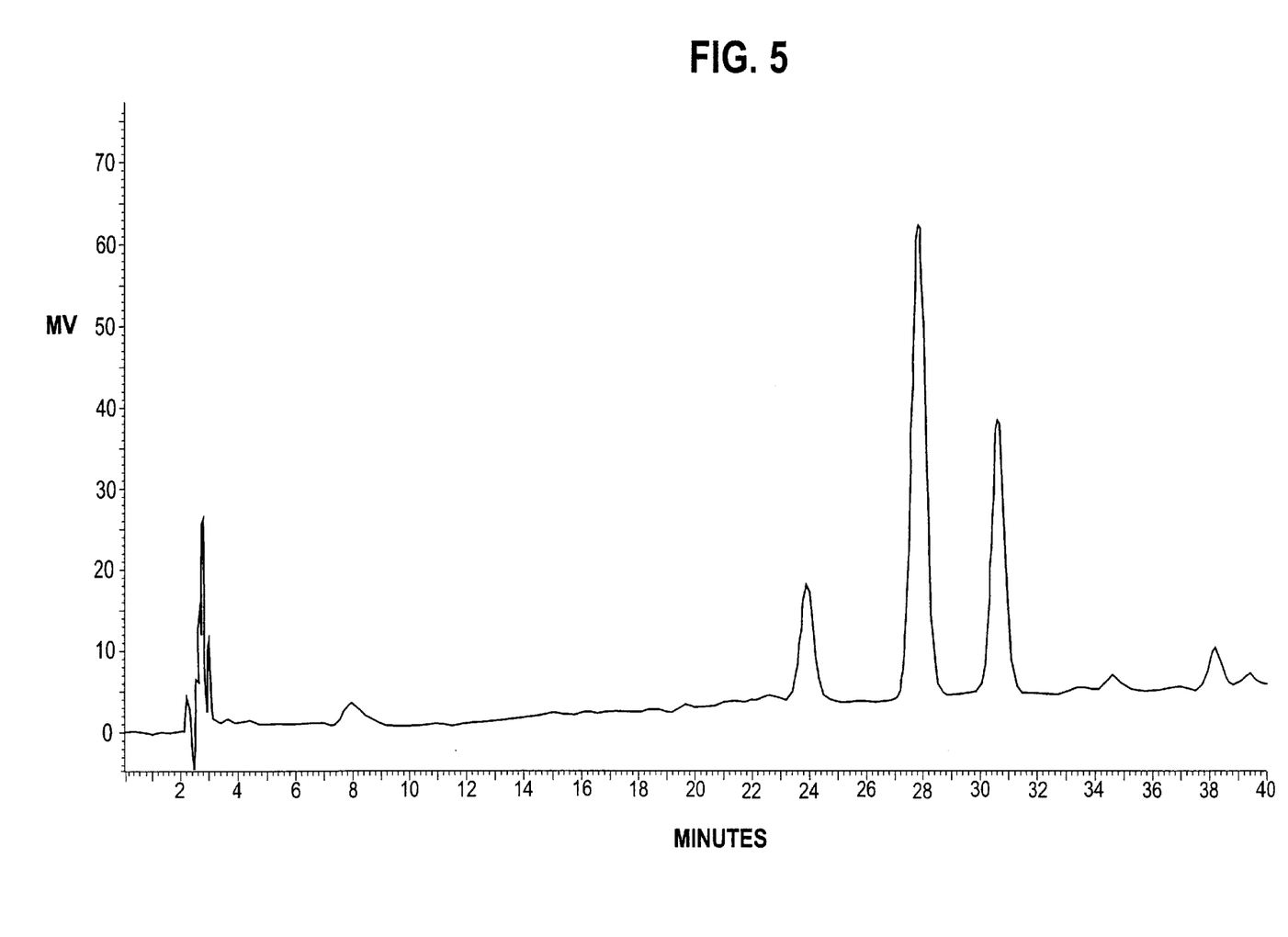
FIG. 5. is a chromatogram showing a separation using the disclosed method using 90% to 100% methanol over 40 minutes.

The chromatograms labeled 98% USP ethanol, 97% USP ethanol, and 95% USP ethanol, corresponding to FIGS. 1, 2, and 3 accordingly, indicate that the separation is enhanced as solvent content in the mobile phase is decreased (all other parameters are constant), provided solubility of product and crude is maintained. 190 proof USP ethanol was used in all process examples discussed herein. Separation enhancement allows for higher loading capacity, but it also increases the elution times of the tocotrienols and tocopherols. The chromatograms labeled 90% to 100% acetonitrile over 40 minutes (FIG. 4) and 90% to 100% methanol over 40 minutes (FIG. 5) indicate that acetonitrile provides better separation than methanol (all other parameters are constant), however methanol or ethanol are preferred as they are safer to work with and is considerably less expensive.

III. Loading

How the chromatography column is loaded with crude material will affect the separation of the final products. The primary goal of process chromatography is to charge the column with as much crude material as possible while maintaining the desired separation of components. This differs from analytical chromatography methods where the goal is to load the smallest amount of material that is needed in order to get an adequate detection of the component eluting from the column.

It has been found that for the preparative isolation of tocotrienols and tocopherols or their isomers, the amount of crude material that can be loaded depends on two main factors. First, the physical characteristics of the crude stock, such as its solubility and specific make-up including the amounts of desired product(s) and the impurities it contains. Second, the desired end product(s) to be produced, for example, if only a class separation of tocotrienols from tocopherols is desired, then the amount of crude material loaded can be much higher that if separation of each of the isomers is desired.

Process Examples

These examples show how different stationary phases can be used to achieve the purification or concentration of tocotrienols and tocopherols and their isomers. Each of these methods has been utilized to isolate several hundred grams of pure materials. Of course, different stationary and mobile phases can be combined other than discussed below, consistent with the methods disclosed herein, as required by the application. 190 proof USP ethanol was used in process examples discussed herein.

The following single step process method was used to provide isolation of tocotrienols and tocopherols and the isomers of these molecules from a palm oil extract using a single column, single step process.

Stationary Phase: 10 μm C18 bonded spherical silica with 100Å pores

Mobile Phase: 90% USP EtOH/10% deionized water

Elution Mode: Isocratic

Linear Velocity: 360 cm/hour

Loading: Approximately 1g of crude extract per 100 g of packing material (1% w/w loading)

Figure 6:
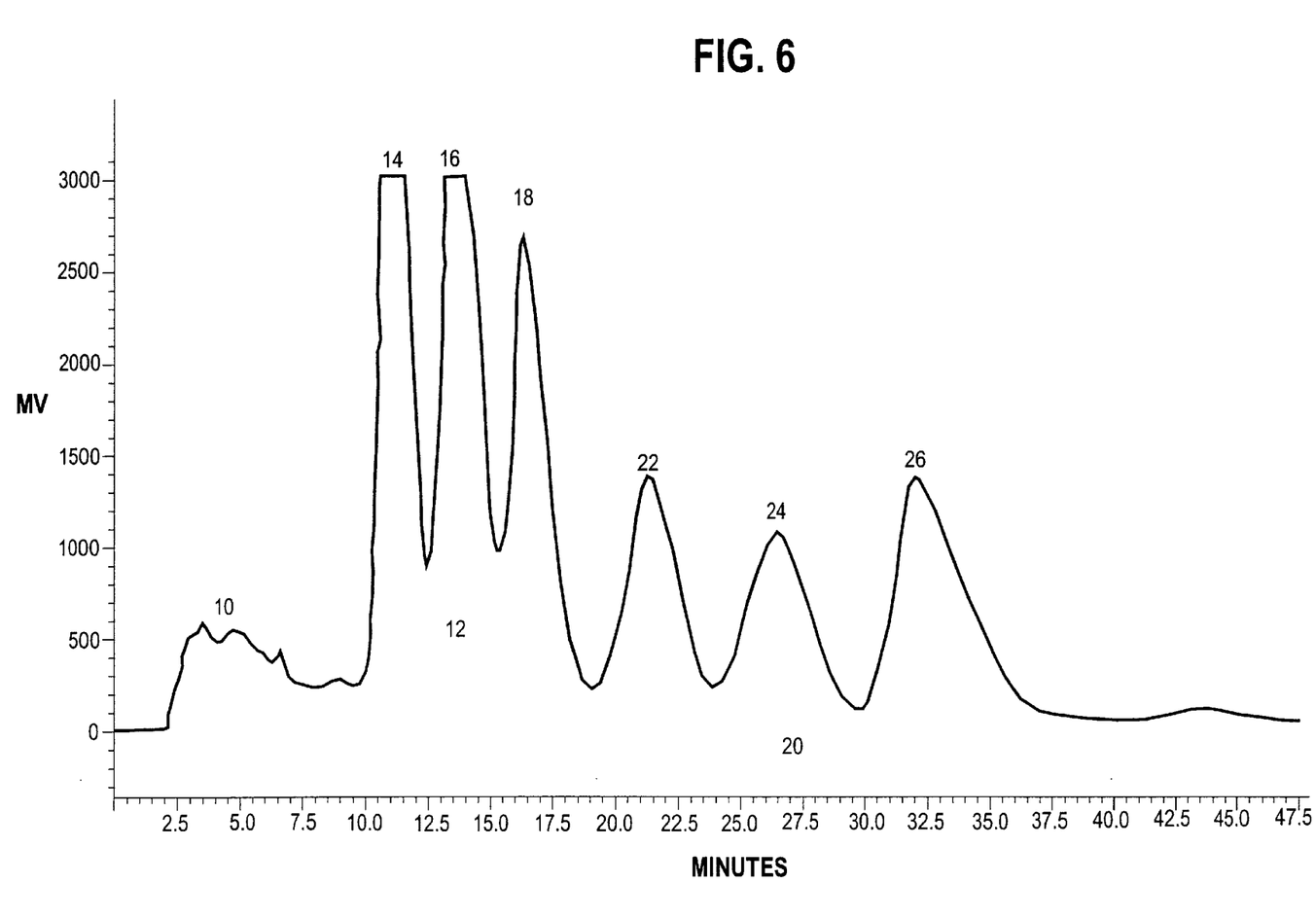
FIG. 6. is a chromatogram showing the results of a separation using a single step process.

The results are shown in FIG. 6. After the elution of some polar impurities 10, the tocotrienols 12 elute with separation of the delta 14, gamma 16, and alpha 18 isomers. The tocopherols 20 elute next with separation of the delta 22, gamma 24, and alpha 26 isomers.

The following two step process method was used to provide isolation of tocotrienols and tocopherols and the isomers of these molecules from a palm oil extract using one or two columns and a two step process. This method is preferred to obtain pure isomers.

Step #1-pre-cleaning of crude to obtain pure tocotrienol or tocopherol mixture

Stationary Phase: 15–35 μm C18 bonded irregular silica with 90Å pores

Mobile Phase: 96% USP EtOH/ 4% deionized water

Elution Mode: Isocratic

Linear Velocity: 42.4 cm/hour

Loading: Approximately 2.7 g of crude extract per 100 g of packing material (2.7% w/w loading)

Figure 7:
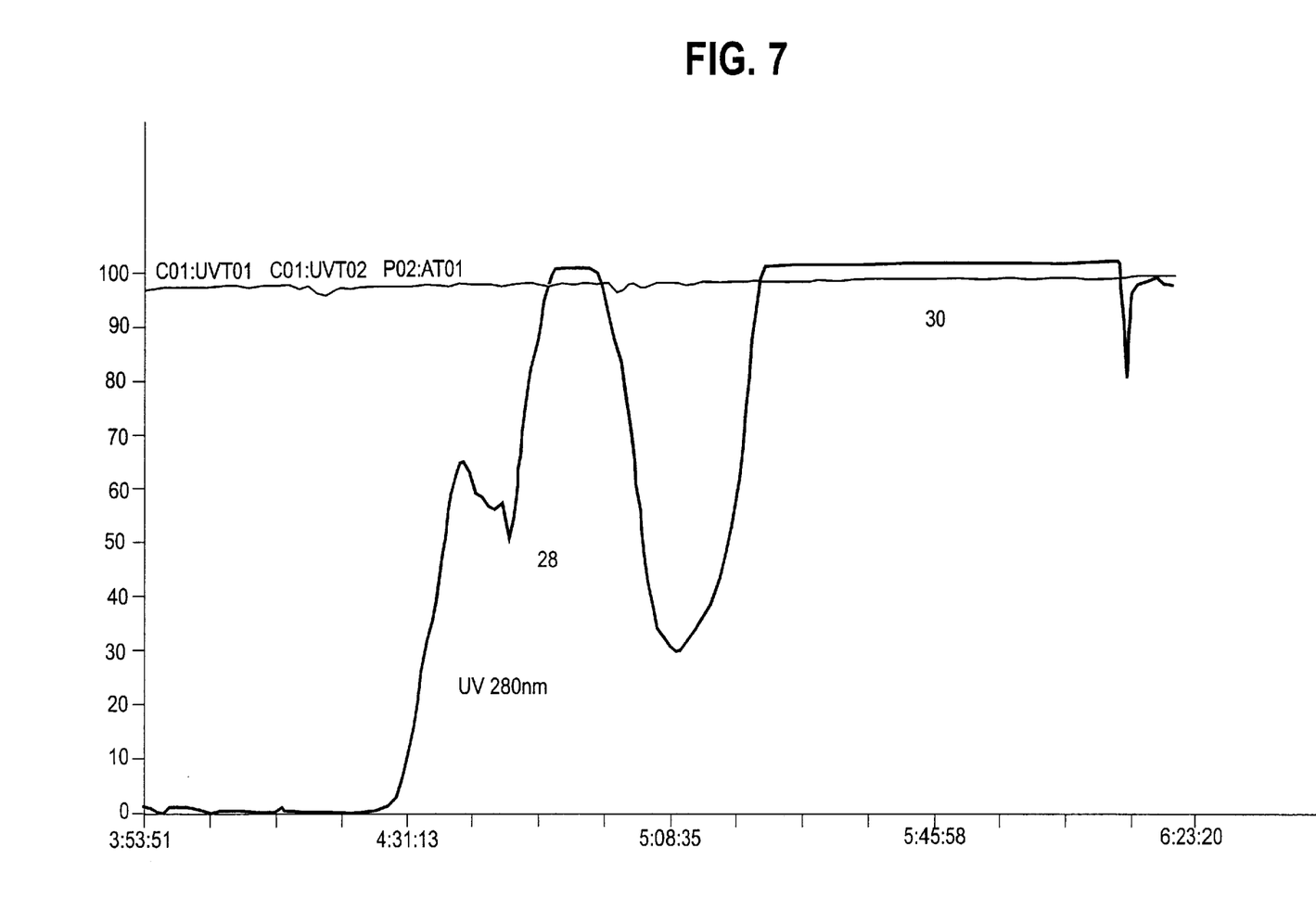
FIG. 7. is a chromatogram showing the results of the first step of a separation using a two step process.

As shown in FIG. 7, after the elution of some polar impurities 28, the tocotrienols 30 elute in one very large band. If the process were continued past the tocotrienol band, the tocopherols would then elute in the same fashion.

Step #2-Overlapped loadings for high throughput of pure isomers

Stationary Phase: 15–35 μm C18 bonded irregular silica with 90 Å pores

Mobile Phase: 96% USP EtOH/4% deionized water

Elution Mode: Isocratic

Linear Velocity: 42.4 cm/hour

Loading: Overlapped loadings—approximately 0.5 g of crude extract per 100 g of packing material (0.5% w/w loading) loaded every 100 minutes.

Figure 8:
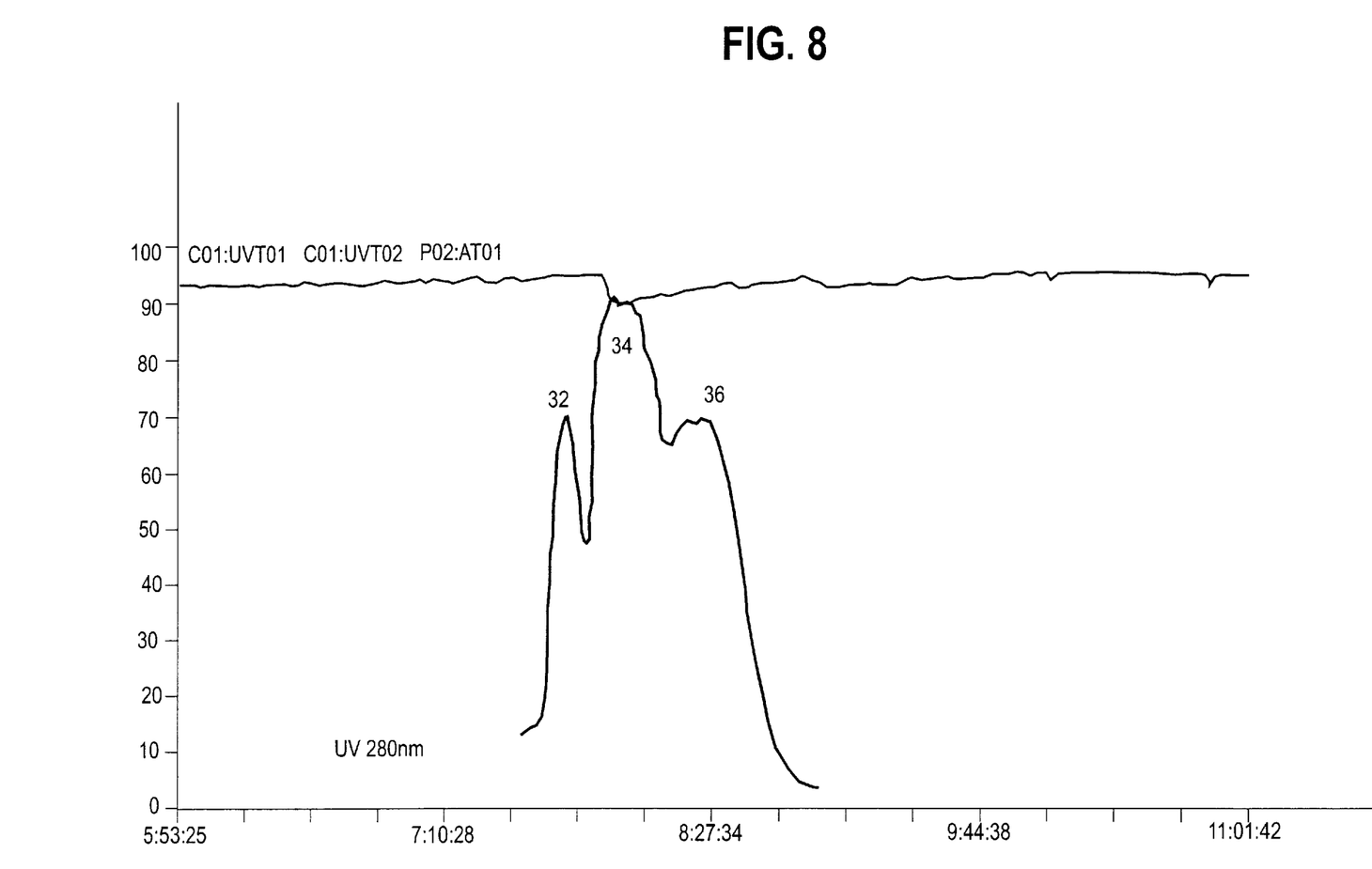
FIG. 8. is a chromatogram showing the results of the second step of a separation using a two step process.

Referring now to FIG. 8, the delta 32, gamma 34, and alpha 36 tocotrienol isomers are well separated. Overlapping the loadings allows for collection of any of the three isomers every 100 minutes for a high throughput continuous process.

In addition to the uses and examples immediately described above, it will be apparent to those skilled in the art that other modifications and variations can be made the method of the instant invention without diverging from the scope, spirit, or teaching of the invention. Therefore, it is the intention of the inventors that the description of instant invention should be considered illustrative and the invention is to be limited only as specified in the claims and equivalents thereto.

We claim:

1. A method of isolating tocotrienols, tocopherols and isomers thereof from a crude initial stock using reverse phase liquid chromatography, the method comprising:

providing a stationary phase selected from the group comprising a hydrophobic or aromatic media;

providing a mobile phase which is capable of solubilizing the crude stock and the tocotrienol and tocopherol end products;

preparing a liquid chromatography column using said stationary phase and said mobile phase;

loading the chromatography column with the crude stock; and eluting the tocotrienols, tocopherols and isomers thereof away from the crude stock.

2. The method of claim 1 wherein the stationary phase is comprised of silica.

3. The method of claim 1 wherein the stationary phase is comprised of spherical particles.

4. The method of claim 1 wherein the stationary phase is comprised of irregular shaped particles.

5. The method of claim 1 wherein the mobile phase comprises an alcohol and water.

6. The method of claim 5 wherein the alcohol comprising the mobile phase is selected from the group comprising ethanol and methanol.

7. The method of claim 5 wherein the water content of the mobile phase is less than 30% of the entire mobile phase.

8. The method of claim 1 wherein the mobile phase comprises acetonitrile and water.

9. The method of claim 5 wherein the concentration of alcohol in relation to the concentration of water in the mobile phase is gradually increased during the elution.

10. A method of isolating tocotrienols, tocopherols and isomers thereof from a crude initial stock by reverse phase liquid chromatography, the method comprising:

providing a stationary phase comprising particles in the range of 10 to 200 micrometers selected from the group comprising hydrophobic or aromatic media;

providing mobile phase which is capable of solubilizing the crude stock and the tocotrienol and tocopherol end products;

preparing a liquid chromatography column using said stationary phase and said mobile phase;

loading the chromatography column with the crude stock; and eluting the tocotrienols, tocopherols and isomers thereof at a relatively constant linear velocity of the mobile phase between 10 cm/hour and 1000 cm/hr.

11. The method of claim 10 wherein the stationary phase is comprised of spherical particles.

12. The method of claim 1 wherein the stationary phase is comprised of 10 to 200 micrometer bonded silica particles;

the mobile phase is comprised of between 70% to 100% ethanol and the elution of the tocotrienols and tocopherols is accomplished at a linear velocity of the mobile phase of between 10 cm/hour to 1000 cm/hour.

13. The method of claim 12 comprising the additional steps of providing a second stationary phase comprising 10–200 micrometer, bonded silica particles;

providing second mobile phase comprised of between 70% to 100% ethanol;

preparing a second liquid chromatography column using said second stationary phase;

loading the second chromatography column with the tocotrienols and tocopherols eluted from the initial separation; and eluting purified tocotrienols or tocopherols and isomers thereof from previously eluted tocotrienols or tocopherols at a relatively constant linear velocity of the mobile phase of between 10 cm/hour and 1000 cm/hr.

14. The method of claim 13 wherein the second chromatography column is loaded with 0.5 grams of the eluted tocotrienols and tocopherols eluted from the initial separation per 100 grams of the stationary phase every 100 minutes in overlapped loadings.

15. The method of claim 10 wherein:

the mobile phase is comprised of 96% USP ethanol;

chromatography column is loaded with 2.7 grams of crude extract per 100 grams of stationary phase; and the elution of the tocotrienols and tocopherols is accomplished at a relatively constant linear velocity of the mobile phase of 42.4 cm/hr.

16. A method of isolating tocotrienols, tocopherols and isomers thereof from a crude initial stock by reverse phase liquid chromatography, the method comprising:

providing a stationary phase comprising 10 micrometer, mono-sized silica spherical particles;

providing mobile phase comprising 90% USP ethanol and 10% water;

preparing a liquid chromatography column using said stationary phase and said mobile phase;

loading the chromatography column with 1 gram of crude stock per 100 grams of the stationary phase; and eluting the tocotrienols, tocopherols and isomers thereof from the crude stock at a relatively constant linear velocity of 360 cm/hour of the mobile phase.

17. The method of claim 10 wherein the stationary phase is comprised of irregular particles.

18. The method of claim 1 wherein the tocotrienols and the tocopherols elute as separate groups.

19. The method of claim 18 further comprising the step of separating the tocotrienols and the tocopherols by simulated moving bed liquid chromatography.

* * * * *